United States Patent [19]

Bossaert

[11] 4,006,627
[45] Feb. 8, 1977

[54] HIGH-SPEED ULTRASONIC ECHO-TOMOGRAPHIC DEVICE

[75] Inventor: Jean Bossaert, Paris, France

[73] Assignee: Thomson-CSF, Paris, France

[22] Filed: Oct. 8, 1975

[21] Appl. No.: 620,913

[30] Foreign Application Priority Data

Oct. 11, 1974  France .............................. 74.34304

[52] U.S. Cl. .............................................. 73/67.8 S
[51] Int. Cl.² ........................................ G01N 29/04
[58] Field of Search ........... 73/67.5 R, 67.5 H, 67.6, 73/67.7, 67.8 R, 67.8 S, 67.9; 178/DIG. 18; 340/5 H, 5 MP; 128/2 V

[56] References Cited

UNITED STATES PATENTS

| | | | |
|---|---|---|---|
| 3,488,438 | 1/1970 | Korpel | 73/67.5 R X |
| 3,723,958 | 3/1973 | Heflinger | 73/67.5 R X |
| 3,763,693 | 10/1973 | Bhuta et al. | 73/67.9 |
| 3,936,791 | 2/1976 | Kossoff | 73/67.8 S X |

*Primary Examiner*—Richard C. Queisser
*Assistant Examiner*—John P. Beauchamp
*Attorney, Agent, or Firm*—Cushman, Darby & Cushman

[57] ABSTRACT

The object of the invention is an ultrasonic echo-tomographic device. An alignment of transducers coupled to the body under observation emits flat ultrasonic radiation. The wave fronts of the echoes received in response at each line parallel to the front of the transducers are transformed by means of an electrical chain, without alteration of phase, in a crystalline medium. A laser and an optical system form by Bragg diffraction the images of these lines which are picked up by a vibrating mirror and projected onto the target of a television camera. The invention is applicable in echo-tomography and enables 1000 images per second to be obtained.

6 Claims, 7 Drawing Figures

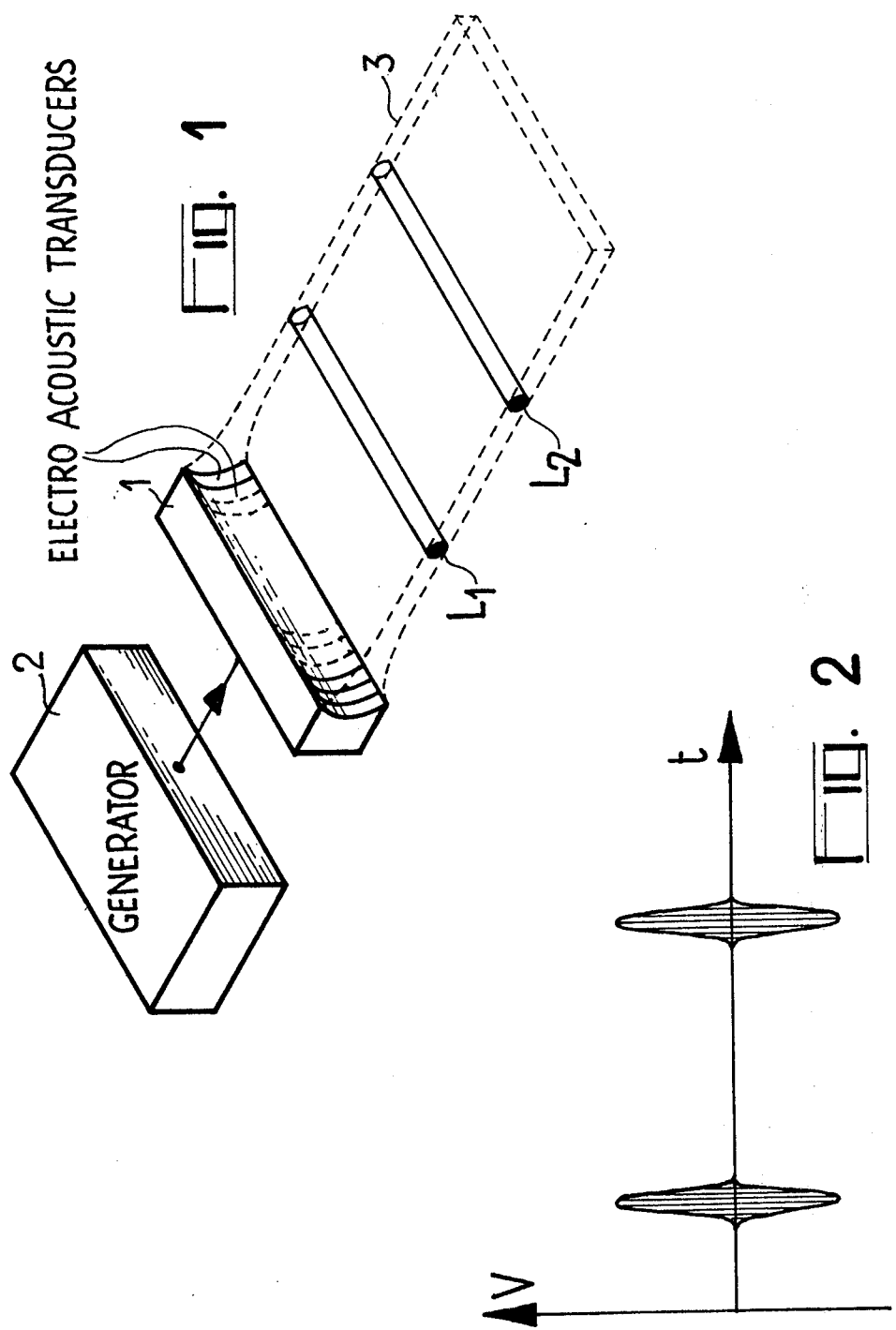

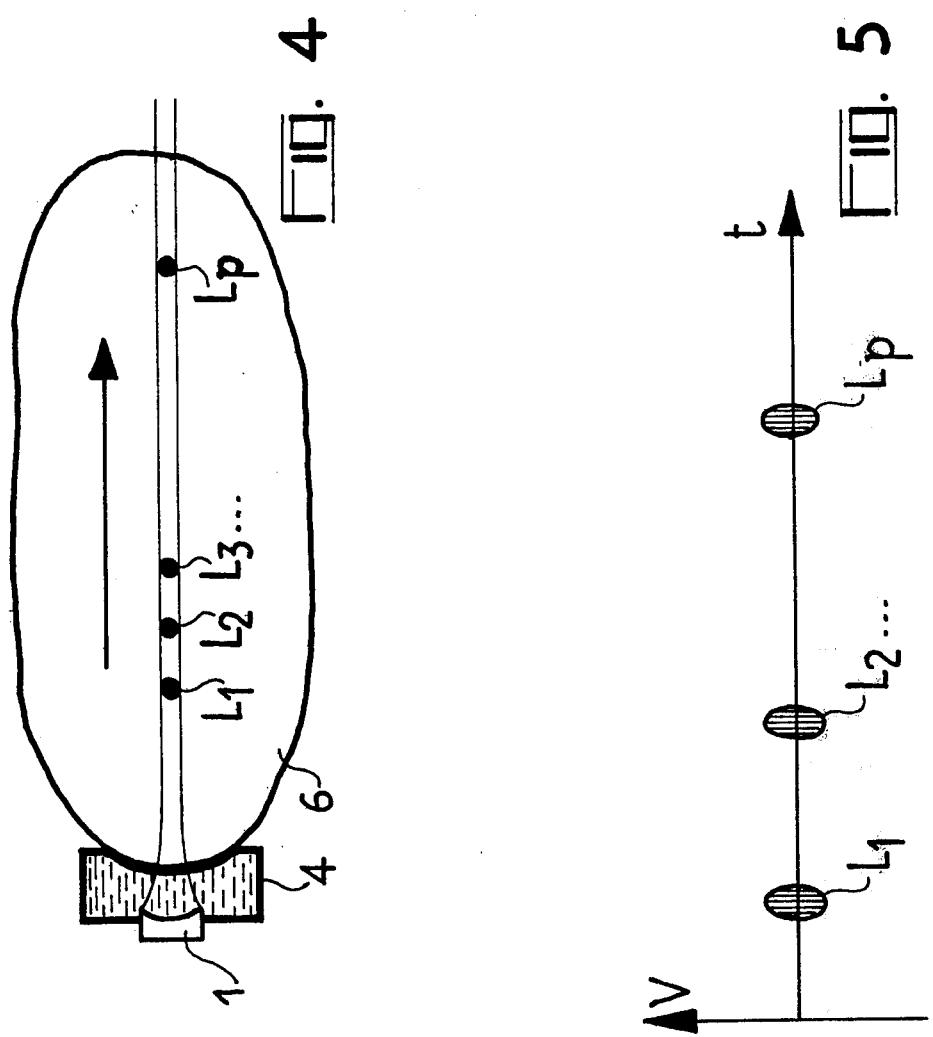

HIGH-SPEED ULTRASONIC ECHO-TOMOGRAPHIC DEVICE

Medical echo-tomography is a method of investigation by which tissues inside the human body are observed. In this method a pulse train of ultrasonic waves is emitted by a transducer having a high directional pattern. The beam that is emitted is very thin. As in radar, for example, echos are radiated by various obstacles in the line of observation. These echos are received by the transducer and an image of the section of the body through which the beam passes is obtained. This image is generally displayed on a storage tube. A tomogram is formed when the transducer is displaced along the body.

This method has several limitations:

a. The resolving power in depth (or ability of separating obstacles close to one another) depends directly on the duration of the wave pulse train. This is what determines the accuracy of the measurement of the time elapsing between emission and reception.

When the duration of the wave pulse trains is limited to two or three half cycles, the resolving power in depth is two or three wavelengths of the ultrasonic wave. As the speed of sound propagation in the body is of the order of 1500m/sec. for a length of one meter, resolving power is of order of 3 centimeters.

b. Transverse resolving power is linked to the diameter of the ultrasonic beam. To obtain a beam of parallel rays, the diameter of the transducer must be somewhat large in relation to that of the wavelength. This diameter must be of the order of 20 wavelengths.

It is, therefore, practically impossible to obtain concentrated beams and this limits transverse resolving power.

Finally, to obtan a complete image, the transducer has to be displaced in order to acquire as many wave pulse trains as lines. The rate of displacement is limited by the speed of propagation of the ultrasounds and it is difficult to obtain more than 15 images per second.

Medical examinations may often require a rate of the order of 100 images per second.

The object of the invention is an echo-tomographic device which allows the same longitudinal resolving power as known apparatus and a much higher rate at which images are obtained.

The ultrasonic echo-tomographic device according to the invention is of the type which has transducers coupled on the body under observation. It is essentially characterised in that it comprises an assembly of aligned transducers capable of emitting simultaneously pulse trains of ultrasonic waves, all the transducers being coupled to the body being studied and the assembly emitting an ultrasonic beam essentially contained in one plane, and electro-optical means enabling the image of the cross section to be regenerated, line by line, parallel to the network of transducers.

The invention will be more easily understood by the following description referring to the attached drawings in which:

FIG. 1 is the basic diagram of a part of a device according to the invention;

FIG. 2 is the electrical signals needed to make tomograms of the body being studied;

FIG. 4 is a cross section of a part of the device in FIG. 3;

FIG. 5 is the echo signals received in response to the signals in FIG. 3;

In FIG. 1 a plurality of electro-acoustic transducers 1, for example one hundred, is arranged in a network and is supplied in phase by a generator 2 of wave pulse trains. The duration of these trains is of the order of a microsecond. The carrier wave can have a frequency of the order of 1 MHz. FIG. 2 shows a succession of such wave trains. The corresponding wavelength must be small enough in relation to the transverse dimension of the transducers to enable them to emit an ultrasonic field 3 of small thickness centred on the plane of longitudinal symmetry of the transducer plurality 1.

Figure 3:
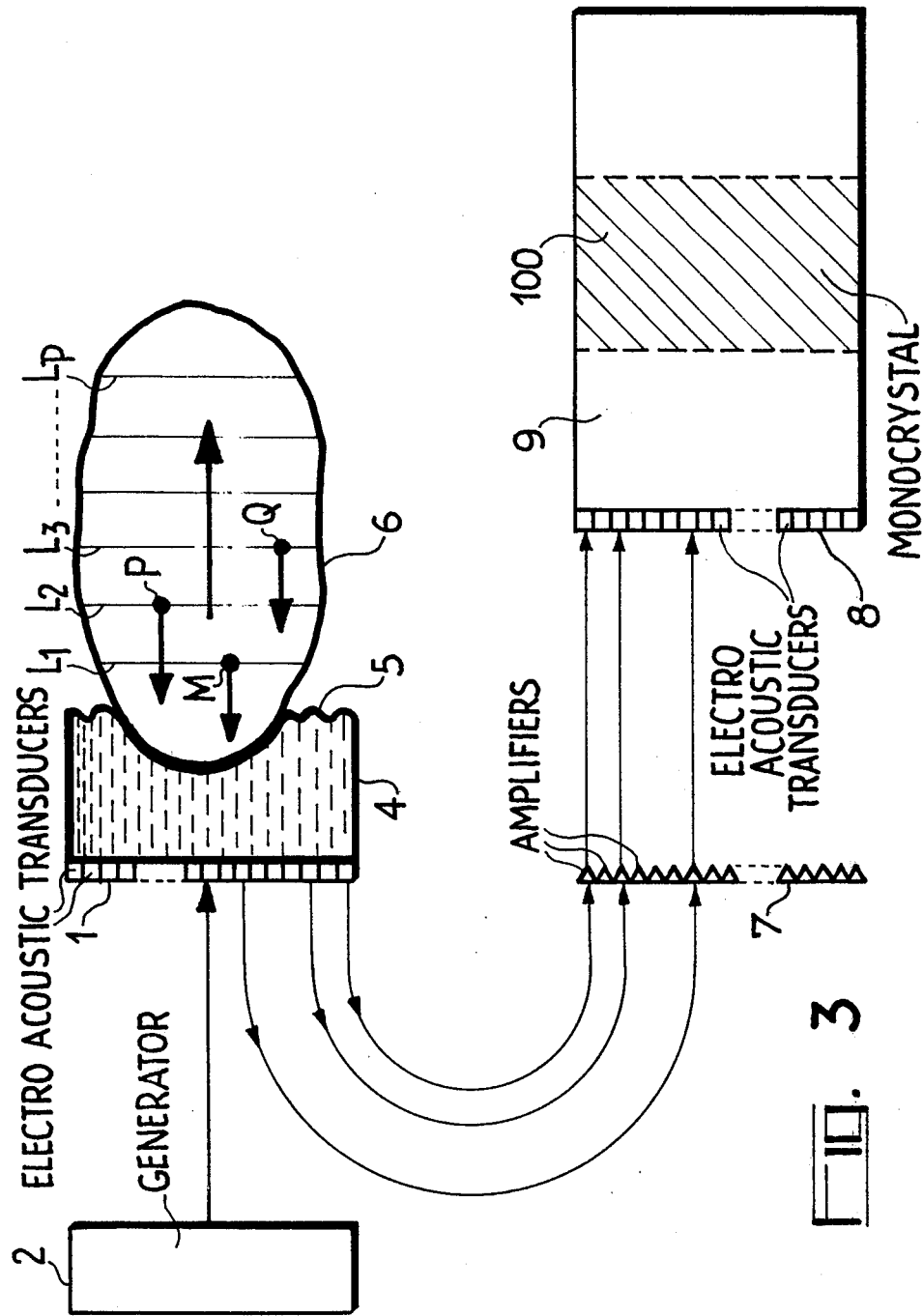
FIG. 3 is a diagram of the device according to the invention.

These transducers 1 (FIG. 3) are coupled to a bag of water 4 sealed by an elastic diaphragm 5 against which the body 6 to be analysed is applied. This body is assumed to be, for example, a portion of an human body. It may be recalled that the speed of sound in the human body is of the order of 1500m/sec., that is, more or less the same as in water, and, consequently, there is no risk of reflections on the interface between the bag of water and the human body.

The element under analysis and the associated transducer assembly are shown in FIG. 4 by a section perpendicular to the plane in FIG. 1.

It will be seen that the assembly 1 is adapted to receive, line by line, $L_1$, $L_2$, $L_p$, the information contained in a clearly defined cross-sectional plane of the body under analysis.

This being so, the transducers 1 emit pulse trains of ultrasonic waves in response to each train of electrical waves (FIG. 4). The result is the displacement in the body 6 of wave planes perpendicular to the plane in FIG. 3 in the direction of the arrow. These wave planes pass through the body along a series of lines $L_1 \ldots L_p$.

In each line each point corresponding to an inhomogeneity in the body (bone or any matter in which the speed of sound propagation is substantially different from the average speed in the remainder of the body) re-emits by radiation a spherical wave $\Sigma$ towards the transducers 1 in response to each wave pulse train. The transducers emit in response the electrical signals in FIG. 5.

These transducers are connected (FIG. 3) respectively to the inputs of a plurality of amplifiers 7, having outputs connected respectively to the inputs of electro-acoustic transducers 8 coupled to the wall of a parallelepiped 9 made of a monocrystal, for example, lead molybdate. This is illuminated by a laser 10, not shown, which emits monochromatic light coherent and concentrated in the hatched area 100.

Figure 6:
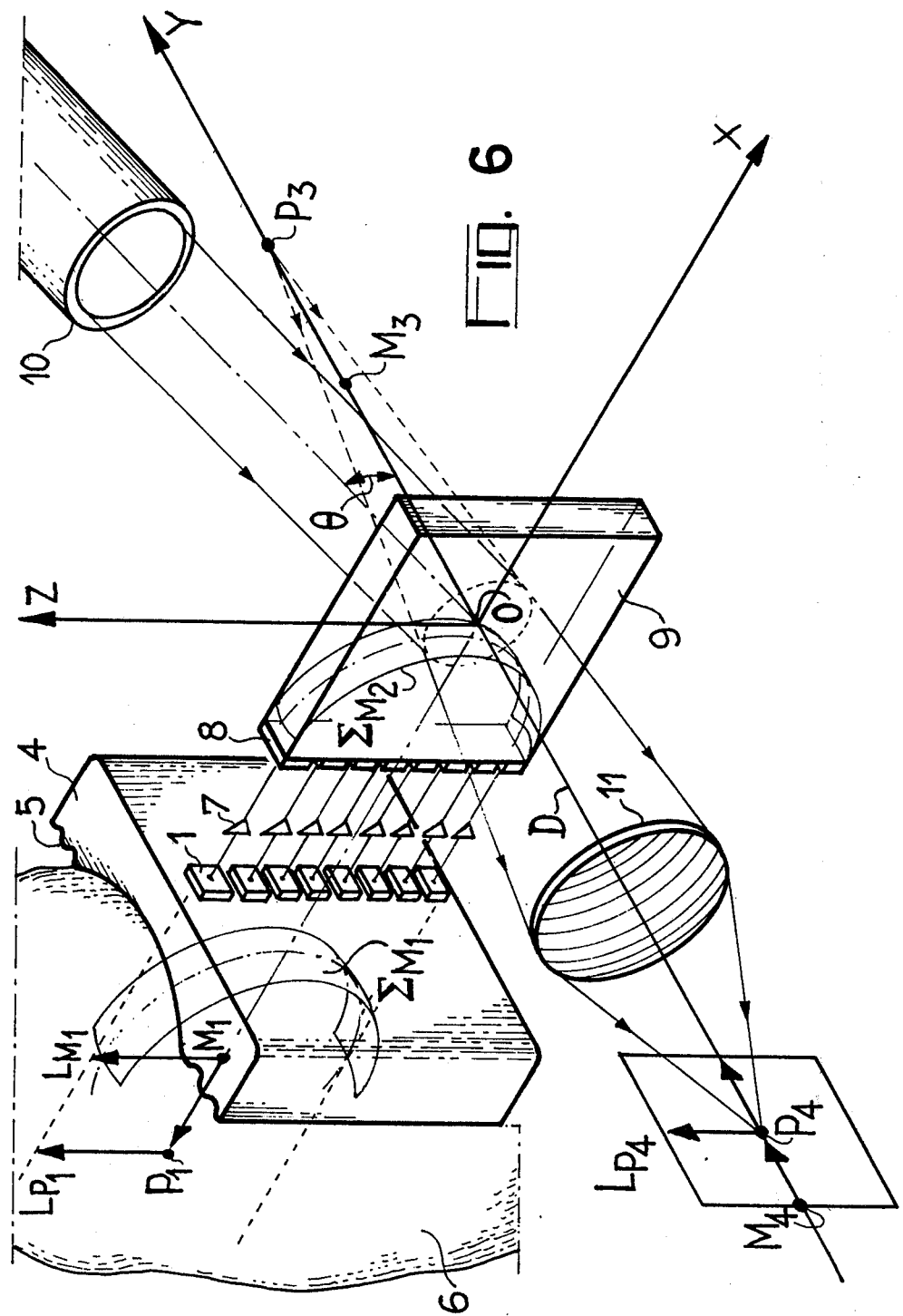
FIG. 6 is a view in perspective of a part of the device according to the invention.

The laser beam is diffracted by the monocrystal in proportion to index variations, collected and used to make the tomogram, as will be seen in FIG. 6 which shows part of the assembly in FIG. 1 in perspective and where the same reference numbers designate the same elements.

This figure shows three axes Oxyz. The axis Ox is the axis along which the ultrasonic waves travel. The edges of the crystal 9 are directed respectively in the directions Ox Oy and Oz; it has a plane of symmetry which is parallel to the plane Oxz. The laser 10 emits a luminous beam of parallel rays, the axis of radiation is parallel to the plane Oyz, and its angle of incidence to the parallelepiped is the Bragg angle $\theta$. It is known that this Bragg angle depends on the substance of the crystal and the wavelength of the laser radiation. The transducers 1 and 8 are in planes parallel to the plane Oyz.

This being so, the effect of the emission of a wave pulse train by the transducers 1 which is propagated in the direction of the arrow is the re-emission by the inhomogeneities in the body 6 of wave pulse trains travelling in the opposite direction and having spherical wave surfaces.

Thus, each point $M_1$ on the axis Ox transmits a wave train in which each wave front can be considered as an approximation as a cylindrical surface $\Sigma$ whose generating lines are parallel to Oy. This wave train is received by the transducers 1 and transmitted electrically to the transducers 8 after amplification in amplifiers 7, the relative phases of the radiation received by each transducer 1 being restored to the transducers 8. Everything takes place, therefore, as if the waves emitted by the point $M_1$ in the body under analysis 6 were emitted by a point $M_2$ located in the crystalline body 9, this point $M_2$ being as far removed from the entry face of the body 9 as the point $M_1$ is from the front of the transducers 1. This wave front $\Sigma_M$ is displaced along the axis Ox in the direction Ox and reaches the crystal portion illuminated by the laser. When attaining this portion, the lower the curvature of the wave front $\Sigma_M$, the higher the distance of point $M_1$ to the straight line transducer alignment, and consequently the distance of virtual point $M_2$ to this illuminated portion. The index of refraction varies synchronously and in proportion to the carrier frequency of the wave trains occurring in the crystal. It can be shown that there results a diffraction of the luminous laser radiation. If the order 1 is selected for this diffraction, it can be shown that there ensues the formation of luminous radiation with a virtual origin at a point $M_3$ located in the plane Oxy; this is a conical radiation whose axis D forms an angle $\theta'$ with the axis Oy which has an aperture $\Delta\theta$, the angles $\theta + \Delta\theta$ and $\theta' - \Delta\theta$ being substantially equal to the Bragg angle. In FIG. 1 for the sake of simplicity, it is assumed that this angle $\theta'$ is equal to O.

Several facts follow from this:

a. all the points $M_1$ on the body which are located on the axis Ox form diffracted radiation whose apparent origin is points $M_3$;

b. the less the bending $f$ of the wave surface when the laser beam passes through, the nearer the point $M_3$ is to the crystal;

c. the points on a line $L_{M1}$ parallel to Oz form a virtual image $L_{M3}$ perpendicular to the axis D.

The result of this is that the points farthest removed from the transducers 1 give virtual images which appear nearer to an observer who is observing the diffracted radiation.

The lens 11 centred on the axis will supply the real images $M_4$ of the points $M_3$ on its optical axis and these images are the nearer to the lens, the farther the virtual points $M_3$ are removed from it.

It must be noted that since the ultrasonic pulse is propagated at a finite speed both in the body being studied and in the crystal, the laser beam will be crossed first by the echos from the points nearest to the transducers 1 and then by those from the farthest points. It follows that the radiation transmitted by the lens 11 will scan a surface located in the plane xOy in the direction of the arrow. The successive lines of the cross section will appear in succession in the plane xOy in the direction of the arrow and the farthest image points (that is, the images of the points nearest to the transducers 1) will appear first.

Figure 7:
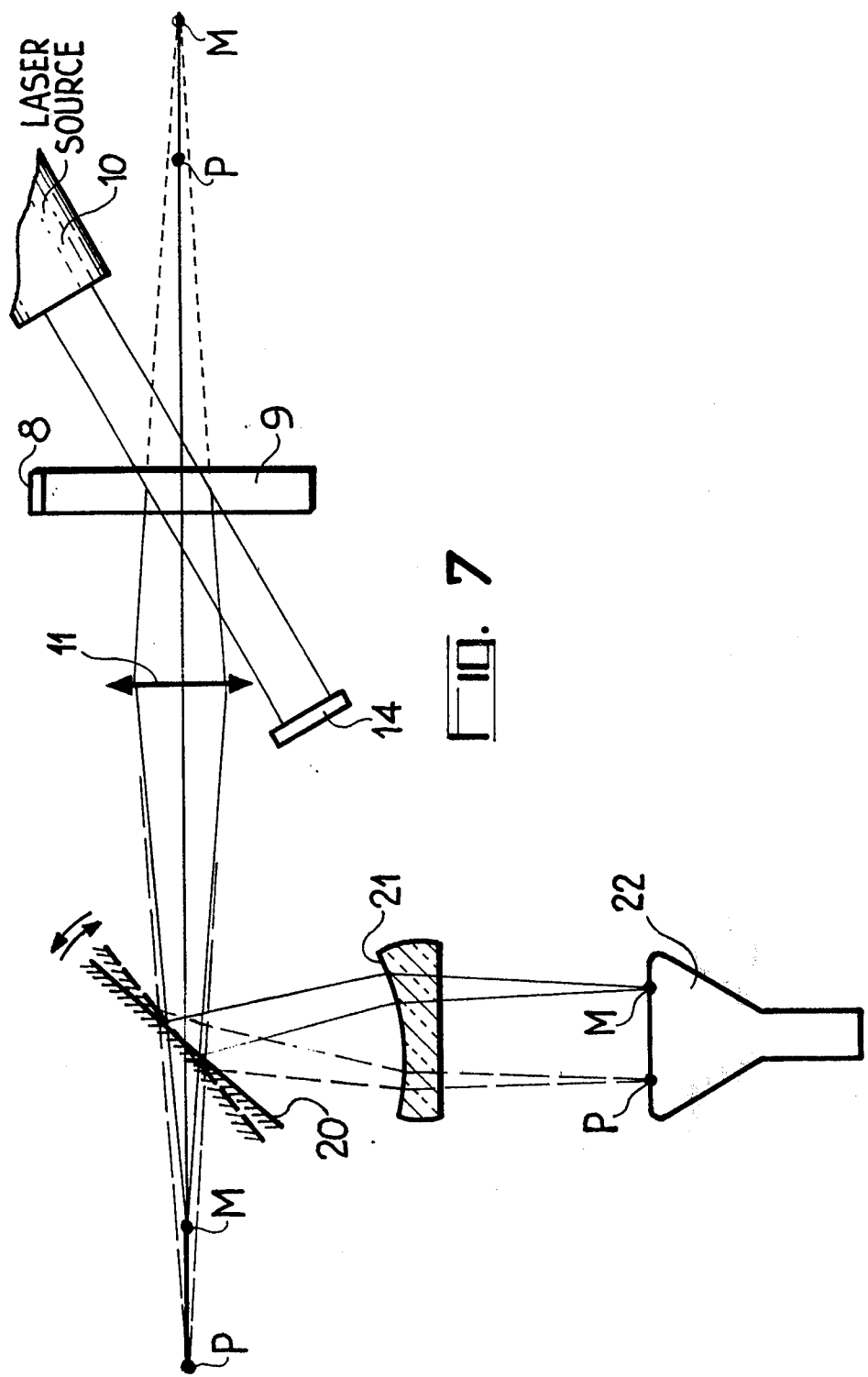
FIG. 7 is a top view of another part of the device according to the invention.

The time taken to scan the image $L_{M1}L_{P1}$ will be equal to twice the time taken for the ultrasonic wave to travel in the body from point $M_1$ to point $P_1$. The image so obtained is difficult to use. In point of fact, if the target of a vidicon is placed in the plane xOy, the luminous rays have a grazing incidence. The line of investigation passing through the point $M_1$ is characterised by the time which elapses between emission and the moment when the corresponding wave front enters the luminous field of the laser. As a result, the various images of the lines of the section succeed one another chronologically at the same spot. To use the image, a vibrating mirror 20 is disposed, as shown in FIG. 7, which projects each line of the tomogram in succession essentially onto the same spot. An optical correcting instrument 21 allows for displacements in the line of observation and its form is chosen so as to form the image on the target of a vidicon. A mask 14 eliminates laser radiation which has not been diffracted. The tomogram takes shape on the target of a vidicon 22 whose optical axis is parallel to the axis Ox. The vibration period of the mirror is equal to twice the time taken by the ultrasound to travel from points $M_1$ to point $P_1$ corresponding to the two ends of the tomogram.

The sole limitation on the number of images per second is the frequency of vibration of the mirror which is a mechanical element. It can reach 1000 cycles per second.

The separating capacity of the tomogram which is obtained by reforming the image optically can attain four wavelengths of the ultrasonic wave in the body being studied.

What we claim is:

1. High speed ultrasonic echo-tomographic system comprising a generator of pulsed wave trains, a first straight line alignment of electroacoustic transducers, supplied in phase by said generator, said first alignment having a longitudinal dimension large in relation to the wavelength of the ultrasonic wave emitted, and coupled to the body being studied, so as to emit a plane shaped beam passing through a cross-section of said body, a second straight line alignment of tranducers electrically connected respectively to said transducers of the first alignment so as to retain the phase of the echo signals received by said first alignment, a crystalline medium, said second alignment being coupled to said crystalline medium to form in reply ultrasonic wave fronts in said medium, an optical system directing a beam of monochromatic light at an incidence substantially equal to the Bragg angle onto the fronts of waves emitted by the second alignment of transducers and optical means to collect one of the orders diffracted by said fronts from the beam emitted by said optical system.

2. Device according to claim 1, wherein said crystalline medium is a rectangular parallelepiped, one of whose end faces supports said second alignment, said second alignment inducing substantially cylindrical wave fronts travelling from the end face to the opposite end face.

3. Device according to claim 2, wherein said optical system is a laser emitting a cylindrical beam whose axis is in a plane parallel to one of the end faces and forms with each wave front an angle substantially equal to the Bragg angle for the wavelength that it emits.

4. Device according to claim 3, wherein said optical means include a converging lens whose optical axis is contained in the plane parallel to the end face and containing the axis of the laser beam and is directed at the Bragg angle corresponding to said order.

5. Device according to claim 4, wherein said optical means comprise a vibrating mirror, a target of a vidicon, and means to direct the images supplied by said lens onto said target.

6. Device according to claim 5, wherein an optical correcting instrument is placed between the vibrating mirror and the target of the vidicon.

* * * * *